(12) United States Patent
Galley et al.

(10) Patent No.: US 7,834,044 B2
(45) Date of Patent: Nov. 16, 2010

(54) SUBSTITUTED-2-IMIDAZOLES

(75) Inventors: Guido Galley, Rheinfelden (DE); Katrin Groebke Zbinden, Liestal (CH); Roger Norcross, Olsberg (CH); Henri Stalder, Basel (CH)

(73) Assignee: Hoffman-LaRoche Inc., Nutley, NJ (US)

( * ) Notice: Subject to any disclaimer, the term of this patent is extended or adjusted under 35 U.S.C. 154(b) by 351 days.

(21) Appl. No.: 11/931,246

(22) Filed: Oct. 31, 2007

(65) Prior Publication Data

US 2008/0113980 A1    May 15, 2008

(30) Foreign Application Priority Data

Nov. 2, 2006  (EP)  ............................ 06123351

(51) Int. Cl.
*A61K 31/427* (2006.01)
*A61K 31/47* (2006.01)
*C07D 215/02* (2006.01)
*C07D 403/06* (2006.01)

(52) U.S. Cl. ............... 514/397; 548/311.1; 548/311.4; 548/312.1; 546/112; 546/152; 514/311; 514/385; 514/396

(58) Field of Classification Search ............ 548/300.1, 548/311.1, 312.1; 546/112, 152; 514/299, 514/311, 385, 397
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Elbe | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 7,211,672 B2 * | 5/2007 | Ghosh et al. | 546/157 |
| 7,504,508 B2 * | 3/2009 | Ghosh et al. | 546/112 |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |

FOREIGN PATENT DOCUMENTS

CA    2246027    2/2000

(Continued)

OTHER PUBLICATIONS

Altenbach et al., Synthesis and Structure-Activity Studies on *N*-[5-(1*H*-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.

(Continued)

*Primary Examiner*—Golam M Shameem
(74) *Attorney, Agent, or Firm*—George W. Johnston; Patricia S. Rocha-Tramaloni; Kimberly J. Prior

(57) ABSTRACT

The present invention relates to compounds of formula I

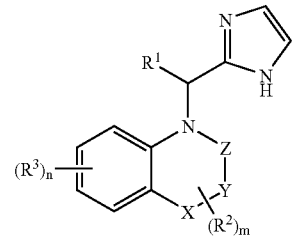

wherein
$R^1$ is selected from the group consisting of hydrogen and lower alkyl;
each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
X is selected from the group consisting of —$CH_2$—, —CH— and —O—;
Y is selected from the group consisting of —$CH_2$—, —CH— and a bond with the proviso that, when X is —O—, Y may not be a bond;
Z is selected from the group consisting of —$CH_2$— and —CH—;
m is 0, 1 or 2; and
n is 0, 1 or 2;
and to pharmaceutically-acceptable acid addition salts of such compounds.

The invention relates also to processes for preparing such compounds, compositions comprising such a compound or a pharmaceutically-acceptable acid addition salt thereof, and a method of treating a disease or disorder in a patient comprising administering such a compound, or pharmaceutically-acceptable acid addition salt thereof, to a patient in need of such treatment.

13 Claims, No Drawings

FOREIGN PATENT DOCUMENTS

| | | |
|---|---|---|
| EP | 323 985 | 12/1966 |
| EP | 0 024 829 | 3/1981 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 857 483 | 8/1998 |
| EP | 0 924 209 | 6/1999 |
| EP | 1 103 243 | 5/2001 |
| EP | 1 413 576 | 4/2004 |
| FR | 6 551 | 12/1968 |
| GB | 877306 | 9/1961 |
| GB | 1016514 | 1/1966 |
| WO | WO 96/22768 | 8/1996 |
| WO | WO 97/12874 | 4/1997 |
| WO | WO 98/12183 | 3/1998 |
| WO | WO 01/30762 A1 | 5/2001 |
| WO | WO 01/81334 | 11/2001 |
| WO | WO 02/22801 A2 | 3/2002 |
| WO | WO 02/40453 A | 5/2002 |
| WO | WO 02/76950 | 10/2002 |
| WO | WO 03/092374 | 11/2003 |
| WO | WO 2004/014898 | 2/2004 |
| WO | WO 2006/119411 | 11/2006 |
| WO | WO 2007/024944 | 3/2007 |
| WO | WO 2007/024949 A2 | 3/2007 |

OTHER PUBLICATIONS

Amemiya et al., Synthesis and α-Adrenergic Activities of 2-and 4-Substituted Imidazoline and Imidazoline Analogues, J. Med. Chem. (1992), 35:750-755.

Bagley et al., Synthesis and $\alpha_2$-Adreneregic Activities of Imidazole and Imidazolidine Analogues: in Vitro and in Vivo Selectivity, Medicinal Chemistry Research (1994), 4:346-364.

Branchek et al., Trace amine receptors as targets for novel therapeutics: legend, myth and fact, Curr. Opin. Phamacol. (2003), 3:90-97.

Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.

Carroll et al., in Vitro and in Vivo Characterization of Alpha-1A Selective Agonists and Their Utility for Stress Incontinence, Med. Chem. Res. (2004), 13:134-148.

De Bernardis et al., Conformationally Defined Adrenergic Agents. 3. Modifications to the Carbocyclic Ring of 5,6-Dihydroxy-1-(2-imidazolinyl)tetralin: Improved Separation of $\alpha_1$ and $\alpha_2$ Adrenergic Activities, J. Med. Chem. (1986), 29:1413-1417.

De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-l-naphthyl)imidazoline: a Potent Agonist at α—Adrenoceptors, J. Med. Chem. (1987), 30:1011-1017.

Faust et al., Antihypertensive Agents: Derivatives of 2-Imidazoline and 1,4,5,6-Tetrahydropyrimidine, J. Org. Chem. (1961), 26: 4044-4047.

Hirashima et al., Three-Dimensional Common-Feature Hypotheses for Octopamine Agonist 2-(Arylimino)imidazolidines, Bioorganic & Medicinal Chemistry (2002), 10:117-123.

Holt, A., Imidazoline binding sites on receptors and enzymes:Emerging targets for novel antidepressant drugs?, Journal of Psychiatry & Neuroscience (2003), 28:409-414.

Jetter et al., Synthesis of 4-Substituted Imidazoles via Palladium-Catalyzed Cross-Coupling Reactions, Synthesis (1998), 829-831.

Law et al., Benzylimidazolines as h5-Htib/Id Serotonin Receptor Ligands: a Structure-Affinity Investigation, J. Med. Chem. (1998), 41:2243-2251.

Lee et al., 4-[(N-Imidazol-2-ylmethyl)aniline]pyranopyridine Analogs as Novel Anti-Angiogenic Agents, Bull. Korean Chem. Soc. (2005), 25: 619-628.

Lindemann et al., A renaissance in trace amines inspired by a novel GPCR family, Trends in Pharmacol. Sci. (2005), 26:274-281.

Lindemann et al., Trace amine-associated receptors form structurally and functionally distinct subfamilies of novel G protein-coupled receptors, Genomics (2005), 85: 372-385.

Matsunaga et al., $C_{17,20}$ inhibitors. Part 2: Design, synthesis and structure-activity relationships of (2- naphthylmethyl)-1H-imidazoles as novel $C_{17,20}$-lyase inhibitors, Bioorganic & Medicinal Chemistry (2004), 4314.

Matsunaga et al., Synthetic studies on (1S)-6,7-dimethoxy-2-naphthyl)-1-(1H-imidazol-4-yl)2-methylpropan-lol as a selective $C_{17,20}$-lyase inhibitor, Tetrahedron: Asymmetry (2004), 15: 2021-2028.

McCormack et al., Autoradiographic Localization of Tryptamine Binding Sites in the Rat and Dog Central Nervous System, J. Neurosci. (1986), 6:94-101.

McLennan, P;L., The Hypothermic Effect of Clonidine and Other Imidazolidines in Relation to their Ability to Enter the Central Nervous System in Mice, European Journal of Pharmacology (1981), 69:477-482.

Mosseau et al., A high-affinity [$^3$H]tryptamine binding site in human brain, Prog. Brain Res. (1995), 106:285-291.

Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.

Ojida et al., Sterocontrolled synthesis of (1S)-1 -(1 H-imidazol-4-yl)-1-(6-methoxy-2-napthyl)-2-methylpropan-1-ol as a potent $C_{17,20}$-lyase inhibitor,Tetrahedron: Asymmetry (2004), 15: 1555-1559.

Olmos et al., Imidazolines stimulate release of insulin from Rin-5AH cells independently from imidazoline $I_1$ and $I_2$ receptors, European Journal of Pharmacology (1994), 262: 41-48.

Prisinzano et al., 2-(aniline)imidazolines and 2-(benzyl)imidazoline derivatives as $h5$-HT$_{1D}$ serotonin receptor ligands, Bioorganic & Medicinal Chemistry Letter (2004), 14:4697-4699.

Savola et al., Cardiovascular and Sedative α-Adrenoceptor Effects of Detomidine-like Arylalkyl Imidazoles and Associated Derivatives, Drug Res. (1988), 38:29-35.

Timmermans et al., Characterization of α-Adrenoceptor Populations. Quantitive Relationships between Cardiovascular Effects Initiated at Central and Peripheral α-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Usdin, E. and M. Sandler, Eds., Psychopharmacology Series, vol. 1: Trace Amines and the Brain (1976), 1-281.

Wentland et al., Syntehsis and Antidepressant Properties of Novel 2-Substituted 4,5-Dihydro-1H-imidazole Derivatives, J. Med. Chem. (1987), 30:1482-1489.

Zhang et al., Medetomidine Analogs as $\alpha_2$-Adreneregic Ligands. 3. Synthesis and Biological Evaluation of a New Series of Medetomidine Analogs and Their Potential Binding Interactions with $\alpha_2$-Adrenoceptors Involving a "Methyl Pocket", J. Med. Chem. (1997), 40: 3014-3024.

* cited by examiner

US 7,834,044 B2

SUBSTITUTED-2-IMIDAZOLES

PRIORITY TO RELATED APPLICATION(S)

This application claims the benefit of European Patent Application No. 06123351.6, filed Nov. 2, 2006, which is hereby incorporated by reference in its entirety.

FIELD OF THE INVENTION

The invention relates to compounds which have a good affinity to the trace amine associated receptors (TAARs), especially for TAAR1. The invention relates also to processes for preparing such compounds, a pharmaceutical composition comprising such a compound, and a method for treating a disease or disorder in a patient comprising administering such a compound to a patient in need of such treatment.

BACKGROUND OF THE INVENTION

The classical biogenic amines (serotonin, norepinephrine, epinephrine, dopamine, histamine) play important roles as neurotransmitters in the central and peripheral nervous system. Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press. Their synthesis and storage, as well as their degradation and reuptake after release are tightly regulated. An imbalance in the levels of biogenic amines is known to be responsible for the altered brain function under many pathological conditions. Wong, M. L. and Licinio, J. (2001) Research and Treatment Approaches to Depression. *Nat. Rev. Neurosci.* 2, 343-351; Carlsson, A. et al. (2001) Interactions Between Monoamines, Glutamate, and GABA in Schizophrenia: New Evidence. *Annu. Rev. Pharmacol. Toxicol.* 41, 237-260; Tuite, P. and Riss, J. (2003) Recent Developments in the Pharmacological Treatment of Parkinson's Disease. *Expert Opin. Investig. Drugs* 12, 1335-1352; Castellanos, F. X. and Tannock, R. (2002) Neuroscience of Attention-deficit/Hyperactivity Disorder: the Search for Endophenotypes. *Nat. Rev. Neurosci.* 3, 617-628.

A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines. Usdin, E. and Sandler, M. eds. (1984), *Trace Amines and the Brain*, Dekker. Their disregulation has been linked to various psychiatric diseases like schizophrenia and depression and for other conditions like attention deficit hyperactivity disorder, migraine headache, Parkinson's disease, substance abuse and eating disorders. Lindemann, L. and Hoener, M. (2005) A Renaissance in Trace Amines Inspired by a Novel GPCR Family. *Trends in Pharmacol. Sci.* 26, 274-281; Branchek, T. A. and Blackburn, T. P. (2003) Trace Amine Receptors as Targets for Novel Therapeutics: Legend, Myth and Fact. *Curr. Opin. Pharmacol.* 3, 90-97; Premont, R. T. et al. (2001) Following the Trace of Elusive Amines. *Proc. Natl. Acad. Sci. U.S.A.* 98, 9474-9475.

For a long time, TA-specific receptors had only been hypothesized based on anatomically discrete high-affinity TA binding sites in the central nervous system of humans and other mammals. Mousseau, D. D. and Butterworth, R. F. (1995) A High-affinity [3H] Tryptamine Binding Site in Human Brain. *Prog. Brain Res.* 106, 285-291; McCormack, J. K. et al. (1986) Autoradiographic Localization of Tryptamine Binding Sites in the Rat and Dog Central Nervous System. *J. Neurosci.* 6, 94-101. Accordingly, the pharmacological effects of TAs were believed to be mediated through the well known machinery of classical biogenic amines, by either triggering their release, inhibiting their reuptake or by "cross-reacting" with their receptor systems. Premont, R. T. et al. (2001) Following the Trace of Elusive Amines. *Proc. Natl. Acad. Sci. U.S.A.* 98, 9474-9475; Dyck, L. E. (1989) Release of Some Endogenous Trace Amines from Rat Striatal Slices in the Presence and Absence of a Monoamine Oxidase Inhibitor. *Life Sci.* 44, 1149-1156; Parker, E. M. and Cubeddu, L. X. (1988) Comparative Effects of Amphetamine, Phenylethylamine and Related Drugs on Dopamine Efflux, Dopamine Uptake and Mazindol Binding. *J. Pharmacol. Exp. Ther.* 245, 199-210. This view changed significantly with the recent identification of several members of a novel family of GPCRs, the trace amine associated receptors (TAARs). Lindemann, L. and Hoener, M. (2005) A Renaissance in Trace Amines Inspired by a Novel GPCR Family. *Trends in Pharmacol. Sci.* 26, 274-281; Lindemann, L. et al. (2005) Trace Amine Associated Receptors form Structurally and Functionally Distinct Subfamilies of Novel G protein-coupled Receptors. *Genomics* 85, 372-385. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies. Lindemann, L. and Hoener, M. (2005) A Renaissance in Trace Amines Inspired by a Novel GPCR Family. *Trends in Pharmacol. Sci.* 26, 274-281; Lindemann, L. et al. (2005) Trace Amine Associated Receptors Form Structurally and Functionally Distinct Subfamilies of Novel G Protein-coupled Receptors. *Genomics* 85, 372-385. TAAR1 is in the first subclass of four genes (TAAR1-4) highly conserved between human and rodents. TAs activate TAAR1 via Gαs. Disregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

The present invention relates to compounds which have a good affinity to the trace amine associated receptors (TAARs), especially for TAAR1.

SUMMARY OF THE INVENTION

The present invention relates to a compound of formula I

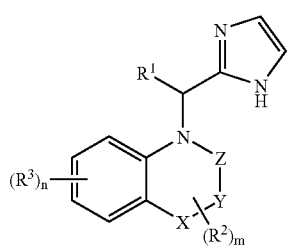

wherein

R¹ is selected from the group consisting of hydrogen and lower alkyl;

each R² is independently selected from the group consisting of hydrogen and lower alkyl;

each R³ is independently selected from the group consisting of hydrogen, lower alkyl, lower alkoxy, phenyloxy, benzyloxy, halogen and lower alkyl substituted by halogen;

X is selected from the group consisting of —CH₂—, —CH— and —O—;

Y is selected from the group consisting of —CH₂—, —CH— and a bond with the proviso that, when X is —O—, Y may not be a bond;

Z is selected from the group consisting of —CH₂— and —CH—;

m is 0, 1 or 2;

n is 0, 1 or 2;

and to a pharmaceutically-acceptable acid addition salt of the above compound.

A further aspect of the present invention are processes for the preparation of the above compound.

Yet another aspect of the present invention is a pharmaceutical composition comprising the above compound or pharmaceutically-acceptable acid addition salt thereof.

Yet another aspect of the present invention is a method for treating a disease or disorder in a patient comprising administering the above compound, or pharmaceutically-acceptable acid addition salt thereof, to a patient in need of such treatment.

DETAILED DESCRIPTION OF THE INVENTION

The present invention relates to a compound of formula I

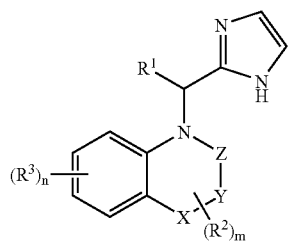

I wherein

R¹ is selected from the group consisting of hydrogen and lower alkyl;

each R² is independently selected from the group consisting of hydrogen and lower alkyl;

each R³ is independently selected from the group consisting of hydrogen, lower alkyl, lower alkoxy, phenyloxy, benzyloxy, halogen and lower alkyl substituted by halogen;

X is selected from the group consisting of —CH₂—, —CH— and —O—;

Y is selected from the group consisting of —CH₂—, —CH— and a bond with the proviso that, when X is —O—, Y may not be a bond;

Z is selected from the group consisting of —CH₂— and —CH—;

m is 0, 1 or 2; and n is 0, 1 or 2;

and to pharmaceutically-acceptable acid addition salts of such a compound.

The invention includes all racemic mixtures, all their corresponding enantiomers and/or optical isomers. In addition, all tautomeric forms of compounds of formula I are also encompassed by the present invention.

Such compounds have a good affinity to the trace amine associated receptors (TAARs), especially for TAAR1 and may be used in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

In preferred embodiments, the compounds of the present invention, or their pharmaceutically-acceptable acid addition salts, are used for treating depression, psychosis, Parkinson's disease, anxiety and attention deficit hyperactivity disorder (ADHD).

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a substituent in which an alkyl group is attached via an oxygen atom to the remainder of the molecule.

As used herein, the term "lower alkyl substituted by halogen" denotes an alkyl group as defined above, wherein at least one hydrogen atom is replaced by halogen, for example CF₃, CHF₂, CH₂F, CH₂CF₃, CH₂CH₂CF₃, CH₂CF₂CF₃ and the like.

The term "halogen" denotes chlorine, iodine, fluorine or bromine.

The term "benzyloxy" refers to a substituent in which a C₆H₅CH₂— group is attached via an oxygen atom to the remainder of the molecule.

The term "phenyloxy" refers to a substituent in which a C₆H₅— group is attached via an oxygen atom to the remainder of the molecule.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of formula I are those wherein X is CH₂, Y is a bond and Z is CH₂.

Such compounds include:

1-(1H-imidazol-2-ylmethyl)-2,3-dihydro-1H-indole;

5-bromo-1-(H-imidazol-2-ylmethyl)-2,3-dihydro-1H-indole;

7-ethyl-1-(1H-imidazol-2-ylmethyl)-2,3-dihydro-1H-indole;

6-chloro-1-(1H-imidazol-2-ylmethyl)-2,3-dihydro-1H-indole;

4-chloro-1-(1H-imidazol-2-ylmethyl)-2,3-dihydro-1H-indole;

1-(1H-imidazol-2-ylmethyl)-7-methoxy-2,3-dihydro-1H-indole;

1-(1H-imidazol-2-ylmethyl)-4-methoxy-2,3-dihydro-1H-indole;
7-chloro-1-(1H-imidazol-2-ylmethyl)-2,3-dihydro-1H-indole;
1-(1H-imidazol-2-ylmethyl)-6-methyl-2,3-dihydro-1H-indole;
1-(1H-imidazol-2-ylmethyl)-7-methyl-2,3-dihydro-1H-indole; and
1-(1H-imidazol-2-ylmethyl)-4-methyl-2,3-dihydro-1H-indole.

Further preferred are compounds of formula I wherein X is CH, Y is a bond and Z is CH, for example the following compound:
(2RS,3RS)-1-(1H-imidazol-2-ylmethyl)-2,3-dimethyl-2,3-dihydro-1H-indole Also preferred are compounds of formula I wherein X is $CH_2$, Y is $CH_2$ and Z is $CH_2$, for example the following compounds:
6-bromo-1-(1H-imidazol-2-ylmethyl)-1,2,3,4-tetrahydro-quinoline;
5-benzyloxy-1-(1H-imidazol-2-ylmethyl)-1,2,3,4-tetrahydro-quinoline; and
1-(1H-imidazol-2-ylmethyl)-5-phenoxy-1,2,3,4-tetrahydro-quinoline.

A further embodiment of the invention are compounds of formula I wherein X is —O—, Y is $CH_2$ and Z is $CH_2$, for example the following compound:
4-(1H-imidazol-2-ylmethyl)-3,4-dihydro-2H-benzo[1,4]oxazine.

Yet another embodiment of the invention are compounds of formula I wherein X is —O—, Y is $CH_2$ and Z is CH, for example the following compound:
(RS)-4-(1H-imidazol-2-ylmethyl)-3-methyl-3,4-dihydro-2H-benzo[1,4]oxazine.

The present compounds of formula I and their pharmaceutically-acceptable acid addition salts can be prepared by methods known in the art, for example, by processes described below.

One such process comprises reductively aminating a compound of formula II

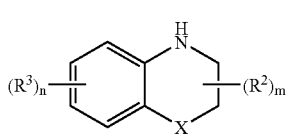

and a compound of formula III

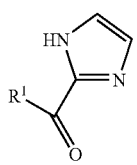

to form a compound of formula I-1

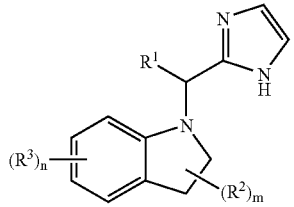

wherein $R^1$, $R^2$, $R^3$, X, m and n are as defined above.

Another such process comprises reductively aminating a compound of formula V

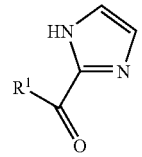

and a compound of formula III

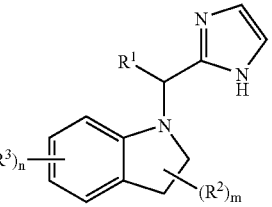

to form a compound of formula I-2

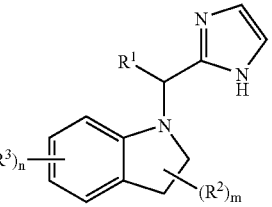

wherein $R^1$, $R^2$, $R^3$, m and n are as defined above.

Yet another such process comprises reductively aminating a compound of formula VII

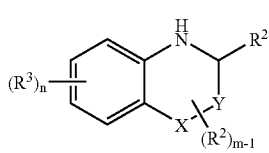

and a compound of formula III

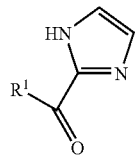

to form a compound of formula I-3

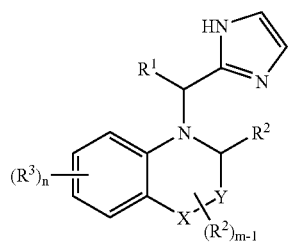

wherein $R^1$, $R^2$, $R^3$, X, Y, m and n are as defined above.

If desired, the compound obtained by one of the processes described above may be converted into a pharmaceutically-acceptable acid addition salt.

The following are general schemes which exemplify the use of the above processes in the production of compounds of formula I. The starting materials are either commercially available, (e.g. from one or more of the following chemical suppliers such as Aldrich, Fluka, Acros, Maybridge, Avocado, TCI, or additional suppliers as indicated in databases such as Chemical Abstracts [American Chemical Society, Columbus, Ohio] or Available Chemicals Directory [Elsevier MDL, San Ramon, Calif.])", are otherwise known in the chemical literature, or may be prepared in accordance with methods described in the specific examples.

Method 1

Scheme 1

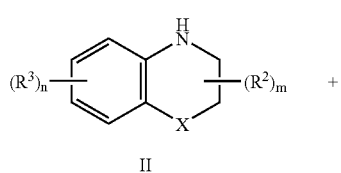

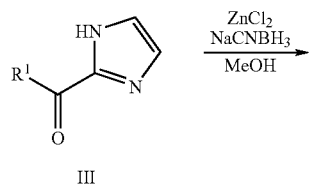

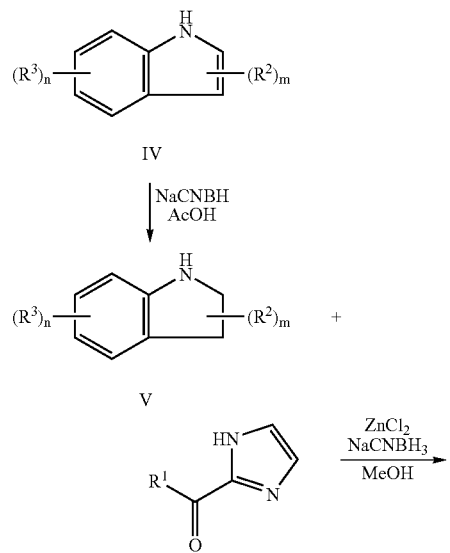

X = O, CH$_2$
$R^1$ = H, alkyl

Compounds of formula I-1 may be prepared by reductive amination using a 1,2,3,4-tetrahydroquinoline (X=CH$_2$) compound or a 3,4-dihydro-2H-benzo[1,4]oxazine (X=O) compound as the amine component and imidazole-2-carboxaldehyde or 2-acetylimidazole as the carbonyl component.

Method 2

Scheme 2

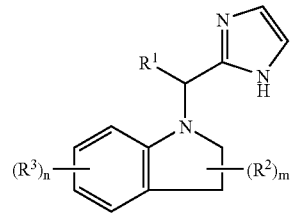

$R^1$ = H, alkyl

Compounds of formula I-2 may be prepared by reductive amination using an indoline compound of formula V as the amine component and imidazole-2-carboxaldehyde or 2-acetylimidazole of formula III as the carbonyl component. The indoline compounds may be prepared by reduction of the corresponding indole analogues in the usual manner.

Method 3

Scheme 3

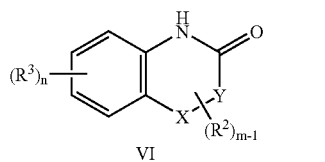

VI i. R²MgCl, THF
ii. NaBH₄, AcOH/THF

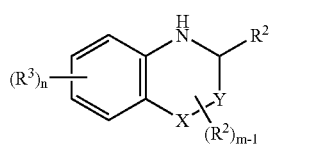

VII

+

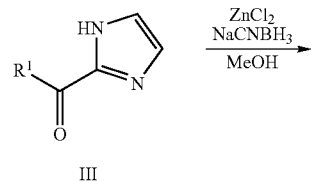

III $\xrightarrow{\substack{ZnCl_2 \\ NaCNBH_3 \\ \hline MeOH}}$

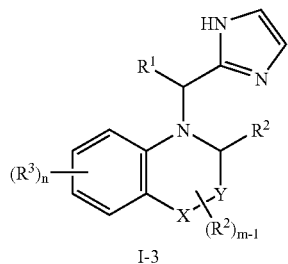

I-3

R¹ = H, alkyl

—X—Y— = —CH₂—, —CH₂—CH₂—, —O—CH₂—

Compounds of formula I-3 may be prepared by reductive amination using an indoline compound (—X—Y—=—CH₂—) or a 1,2,3,4-tetrahydroquinoline compound (—X—Y—=—CH₂—CH₂—) or a 3,4-dihydro-2H-benzo[1,4]oxazine compound (—X—Y—=—O—CH₂—) as the amine component (VII) and imidazole-2-carboxaldehyde or 2-acetylimidazole as the carbonyl component (III). The amino compounds can be prepared from the corresponding 1,3-dihydro-indol-2-one compound (—X—Y—=—CH₂—) or a 3,4-dihydro-2(1H)-quinolinone compound (—X—Y—=—CH₂—CH₂—) or a 2H-1,4-benzoxazin-3(4H)-one compound (—X—Y—=—O—CH₂—) by addition of a Grignard reagent followed by reduction in the usual manner.

Method 4

Scheme 4

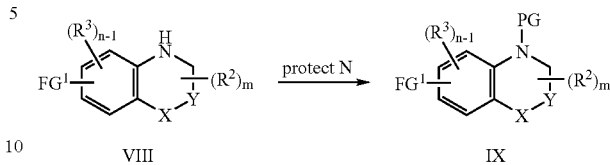

functional group transformation
FG1→FG2

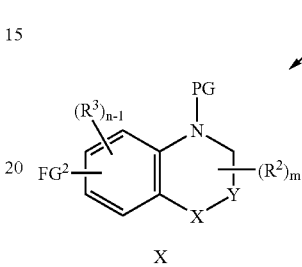

X de-protect N

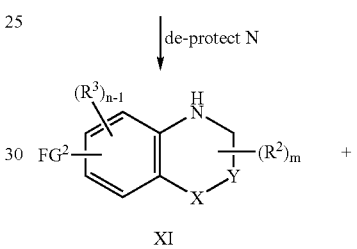

XI

+

III $\xrightarrow{\substack{ZnCl_2 \\ NaCNBH_3 \\ \hline MeOH}}$

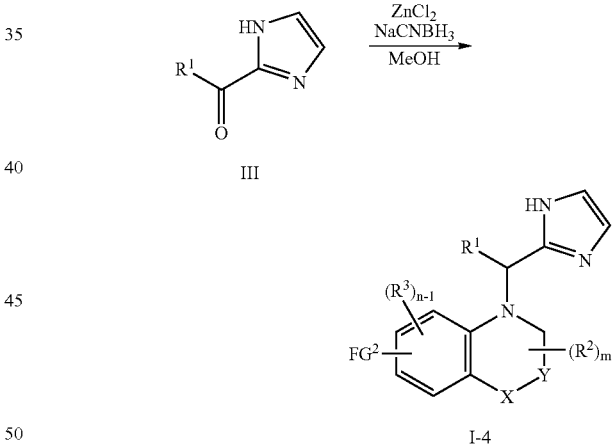

I-4

R¹ = H, alkyl

—X—Y— = —CH₂—, —CH₂—CH₂—, —O—CH₂—

PG = a nitrogen protecting group stable to conditions used to transform FG¹ into FG², e.g. tert-butoxycarbonyl (BOC)

In cases where the amino starting material bears a reactive functional group (e.g. a free hydroxy group) on the aryl ring, it may be possible to perform a functional group transformation before carrying out the reductive amination step. In order to carry out the desired functional group transformation it will frequently prove advantageous to first protect the nitrogen atom which is subsequently required to participate in the reductive amination step. For instance, this nitrogen atom may be protected by conversion to a tert-butyl carbamate moiety. Examples of functional group transformations include common functional group transformations already described in the chemical literature, such as transformation of $FG^1$=hydroxy to $FG^2$=alkyl ether by treatment with a base such as sodium hydride and an alkylating agent such as an alkyl halide. Another possible functional group transformation is the transformation of $FG^1$=hydroxy to $FG^2$=aryl ether by treatment with an aryl boronic acid and copper(II) acetate according to the method of Evans et al. (*Tetrahedron Lett.* 1998, 39, 2937-2940).

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically-acceptable acid addition salts possess valuable pharmacological properties. Specifically, it has been found that the compounds of the present invention have a good affinity to the trace amine associated receptors (TAARs), especially TAAR1.

Compositions containing a compound of formula I or a pharmaceutically-acceptable acid addition salt thereof and a therapeutically inert carrier are also an object of the present invention, as is a process for their production, which comprises bringing one or more compounds of formula I and/or pharmaceutically acceptable acid addition salts thereof and, if desired, one or more other therapeutically valuable substances into a galenical administration form together with one or more therapeutically inert carriers.

The pharmaceutical compositions can be administered orally, e.g. in the form of tablets, coated tablets, dragées, hard and soft gelatine capsules, solutions, emulsions or suspensions. The administration can also be effected rectally, e.g. in the form of suppositories, and parenterally, e.g. in the form of injection solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance, no carriers are usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically-valuable substances.

The present invention relates also to a method for treating a disease or disorder in a patient comprising administering a therapeutically-effective amount of a compound of the present invention to a patient in need of such treatment. A "therapeutically-effective amount" is the amount of the subject compound that will elicit the biological or medical response of a tissue, system, animal or human that is being sought by the researcher, veterinarian, medical doctor or other clinician. The above method may involve the administration of a composition which comprises a therapeutically-effective amount of the compound such as the compositions described above.

In preferred embodiments, the compound is used to treat disorders of the central nervous system, for example the treatment or prevention of depression, psychosis, Parkinson's disease, anxiety and attention deficit hyperactivity disorder (ADHD).

The therapeutically-effective amount can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Item | Ingredients | Tablet Formulation (Wet Granulation) mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLES

The following examples illustrate the invention but are not intended to limit its scope.

Example 1

1-(1H-Imidazol-2-ylmethyl)-2,3-dihydro-1H-indole

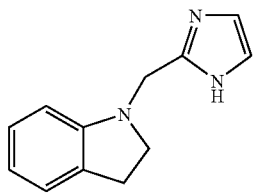

To a solution of indoline (0.20 g, 1.68 mmol) in methanol (15 ml) were added sequentially imidazole-2-carboxaldehyde (0.24 g, 2.52 mmol), zinc chloride (0.92 g, 6.71 mmol) and sodium cyanoborohydride (0.32 g, 5.03 mmol). The reaction mixture was shaken at 50° C. for 16 hours, then triethylamine (0.5 ml) was added and the mixture shaken for a further 5 min. The resulting suspension was filtered and the filtrate was concentrated in vacuo. The residue was purified by chromatography on silica gel (eluant: methanol/dichloromethane gradient) to yield the title compound as an off-white solid (0.17 g, 52%); MS (ISP): 200.3 ([M+H]$^+$).

Example 2

(RS)-1-(1H-Imidazol-2-ylmethyl)-2-methyl-2,3-dihydro-1H-indole

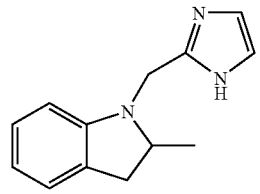

Analogously to Example 1, the above compound was obtained from (RS)-2-methylindoline, imidazole-2-carboxaldehyde, zinc chloride and sodium cyanoborohydride in methanol. MS (ISP): 214.3 ([M+H]$^+$).

Example 3

(RS)-1-[1-(H-Imidazol-2-yl)-ethyl]-2,3-dihydro-1H-indole

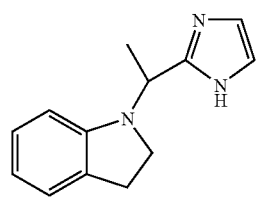

Analogously to Example 1, the above compound was obtained from indoline, 2-acetylimidazole, zinc chloride and sodium cyanoborohydride in methanol. MS (ISP): 214.4 ([M+H]$^+$).

Example 4

5-Bromo-1-(1H-imidazol-2-ylmethyl)-2,3-dihydro-1H-indole

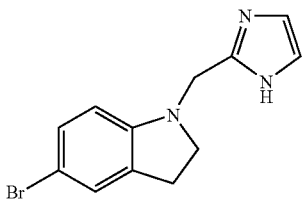

Analogously to Example 1, the above compound was obtained from 5-bromoindoline, imidazole-2-carboxaldehyde, zinc chloride and sodium cyanoborohydride in methanol. MS (ISP): 280.0 ([$^{81}$Br}M+H]$^+$), 278.1 ([$^{79}$Br}M+H]$^+$).

Example 5

1-(1H-Imidazol-2-ylmethyl)-6-trifluoromethyl-2,3-dihydro-1H-indole

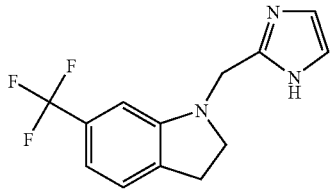

Analogously to Example 1, the above compound was obtained from 6-(trifluoromethyl)indoline, imidazole-2-carboxaldehyde, zinc chloride and sodium cyanoborohydride in methanol. MS (ISP): 268.1 ([M+H]+.

Example 6

5-Chloro-1-(1H-imidazol-2-ylmethyl)-2,3-dihydro-1H-indole

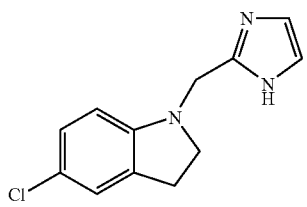

Analogously to Example 1, the above compound was obtained from 5-chloroindoline, imidazole-2-carboxaldehyde, zinc chloride and sodium cyanoborohydride in methanol. MS (ISP): 236.1 ([{37Cl}M+H]+), 234.1 ([{35Cl}M+H]+).

Example 7

(RS)-5-Chloro-1-(1H-imidazol-2-ylmethyl)-2-methyl-2,3-dihydro-1H-indole

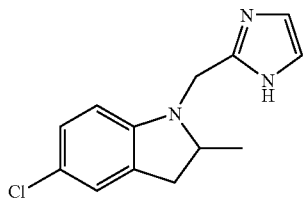

(a) (RS)-5-Chloro-2-methyl-2,3-dihydro-1H-indole

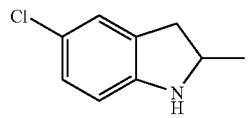

To a solution of 5-chloro-2-methylindole (1.00 g, 6.04 mmol) in acetic acid (7 ml) was added portionwise sodium cyanoborohydride (0.76 g, 12.1 mmol) and the reaction mixture was stirred at room temperature for 16 hours. The resulting solution was diluted with ethyl acetate and washed sequentially with water and with 5 N aq. sodium hydroxide solution. The organic phase was dried over sodium sulphate and concentrated in vacuo. The residue was purified by chromatography on silica gel (eluant: heptane/ethyl acetate gradient) to yield the title compound as a colourless oil (1.00 g, 100%); MS (ISP): 170.2 ([{37Cl}M+H]+), 168.3 ([{35Cl}M+H]+).

(b) (RS)-5-Chloro-1-(1H-imidazol-2-ylmethyl)-2-methyl-2,3-dihydro-1H-indole

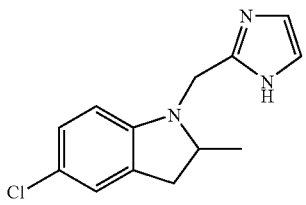

Prepared analogously to Example 1, from 5-chloro-2-methyl-2,3-dihydro-1H-indole, imidazole-2-carboxaldehyde, zinc chloride and sodium cyanoborohydride in methanol. MS (ISP): 250.1 ([{37Cl}M+H]+), 248.2 ([{35Cl}M+H]+).

Example 8

1-(1H-Imidazol-2-ylmethyl)-1,2,3,4-tetrahydro-quinoline

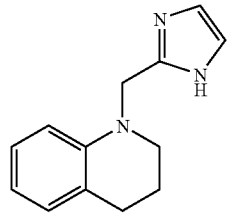

Analogously to Example 1, the above compound was obtained from 1,2,3,4-tetrahydroquinoline, imidazole-2-carboxaldehyde, zinc chloride and sodium cyanoborohydride in methanol. MS (ISP): 214.3 ([M+H]+).

Example 9

(RS)-1-(1H-Imidazol-2-ylmethyl)-2-methyl-1,2,3,4-tetrahydro-quinoline

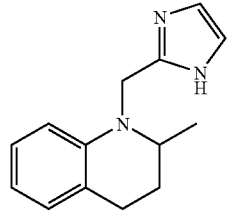

Analogously to Example 1, the above compound was obtained from (RS)-1,2,3,4-tetrahydroquinaldine, imidazole-2-carboxaldehyde, zinc chloride and sodium cyanoborohydride in methanol. MS (ISP): 228.4 ([M+H]+).

Example 10

(RS)-6-Fluoro-1-(1H-imidazol-2-ylmethyl)-2-methyl-1,2,3,4-tetrahydro-quinoline

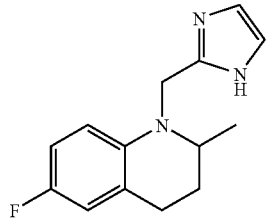

Analogously to Example 1, the above compound was obtained from (RS)-6-fluoro-2-methyl-1,2,3,4-tetrahydroquinoline, imidazole-2-carboxaldehyde, zinc chloride and sodium cyanoborohydride in methanol. MS (ISP): 246.3 ([M+H]+).

Example 11

4-(1H-Imidazol-2-ylmethyl)-3,4-dihydro-2H-benzo[1,4]oxazine

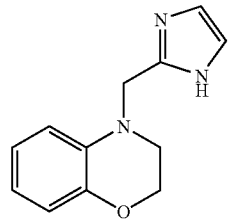

Analogously to Example 1, the above compound was obtained from 3,4-dihydro-2H-benzo[1,4]oxazine, imidazole-2-carboxaldehyde, zinc chloride and sodium cyanoborohydride in methanol. MS (ISP): 216.4 ([M+H]+).

Example 12

(RS)-5-Bromo-1-[1-(1H-imidazol-2-yl)-ethyl]-2,3-dihydro-1H-indole

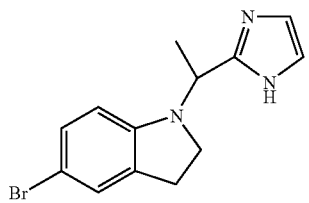

Analogously to Example 1, the above compound was obtained from 5-bromoindoline, 2-acetylimidazole, zinc chloride and sodium cyanoborohydride in methanol. MS (ISP): 294.0 ([{81Br}M+H]+), 292.0 ([{79Br}M+H]+).

Example 13

(RS)-5-Chloro-1-[1-(1H-imidazol-2-yl)-ethyl]-2,3-dihydro-1H-indole

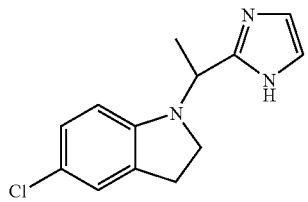

Analogously to Example 1, the above compound was obtained from 5-chloroindoline, 2-acetylimidazole, zinc chloride and sodium cyanoborohydride in methanol. MS (ISP): 250.1 ([{37Cl}M+H]+), 248.2 ([{35Cl}M+H]+).

Example 14

(2RS,3RS)-1-(1H-Imidazol-2-ylmethyl)-2,3-dimethyl-2,3-dihydro-1H-indole

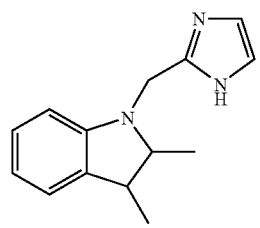

Analogously to Example 7, the above compound was obtained from 2,3-dimethylindole and sodium cyanoborohydride in acetic acid, then treatment with imidazole-2-carboxaldehyde, zinc chloride and sodium cyanoborohydride in methanol. MS (ISP): 228.1 ([M+H]+).

Example 15

7-Ethyl-1-(1H-imidazol-2-ylmethyl)-2,3-dihydro-1H-indole

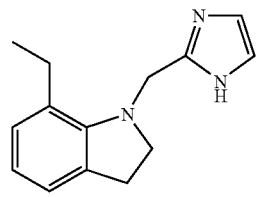

Analogously to Example 7, the above compound was obtained from 7-ethylindole and sodium cyanoborohydride in acetic acid, then treatment with imidazole-2-carboxaldehyde, zinc chloride and sodium cyanoborohydride in methanol. MS (ISP): 228.4 ([M+H]+).

Example 16

6-Chloro-1-(1H-imidazol-2-ylmethyl)-2,3-dihydro-1H-indole

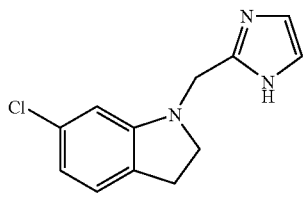

Analogously to Example 7, the above compound was obtained from 6-chloroindole and sodium cyanoborohydride in acetic acid, then treatment with imidazole-2-carboxaldehyde, zinc chloride and sodium cyanoborohydride in methanol. MS (ISP): 236.2 ([{$^{37}$Cl}M+H]$^+$), 234.1 ([{$^{35}$Cl}M+H]$^+$).

Example 17

4-Chloro-1-(1H-imidazol-2-ylmethyl)-2,3-dihydro-1H-indole

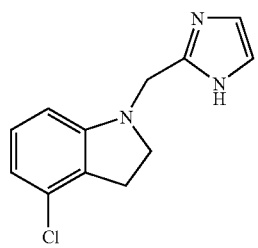

Analogously to Example 7, the above compound was obtained from 4-chloroindole and sodium cyanoborohydride in acetic acid, then treatment with imidazole-2-carboxaldehyde, zinc chloride and sodium cyanoborohydride in methanol. MS (ISP): 236.2 ([{$^{37}$Cl}M+H]$^+$), 234.1 ([{$^{35}$Cl}M+H]$^+$).

Example 18

1-(1H-Imidazol-2-ylmethyl)-5-methoxy-2,3-dihydro-1H-indole

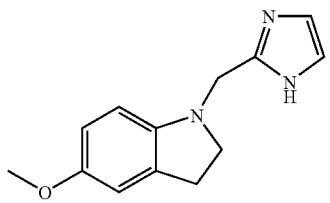

Analogously to Example 7, the above compound was obtained from 5-methoxyindole and sodium cyanoborohydride in acetic acid, then treatment with imidazole-2-carboxaldehyde, zinc chloride and sodium cyanoborohydride in methanol. MS (ISP): 230.3 ([M+H]$^+$).

Example 19

1-(1H-Imidazol-2-ylmethyl)-6-methoxy-2,3-dihydro-1H-indole

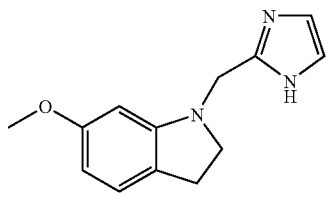

Analogously to Example 7, the above compound was obtained from 6-methoxyindole and sodium cyanoborohydride in acetic acid, then treatment with imidazole-2-carboxaldehyde, zinc chloride and sodium cyanoborohydride in methanol. MS (ISP): 230.4 ([M+H]$^+$).

Example 20

1-(1H-Imidazol-2-ylmethyl)-7-methoxy-2,3-dihydro-1H-indole

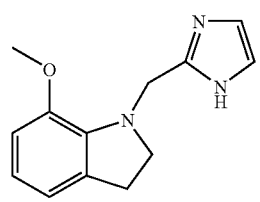

Analogously to Example 7, the above compound was obtained from 7-methoxyindole and sodium cyanoborohydride in acetic acid, then treatment with imidazole-2-carboxaldehyde, zinc chloride and sodium cyanoborohydride in methanol. MS (ISP): 230.4 ([M+H]$^+$).

Example 21

1-(1H-Imidazol-2-ylmethyl)-5-methyl-2,3-dihydro-1H-indole

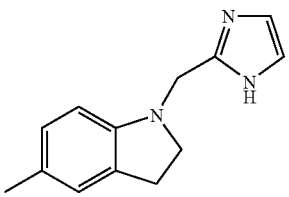

Analogously to Example 7, the above compound was obtained from 5-methylindole and sodium cyanoborohydride in acetic acid, then treatment with imidazole-2-carboxaldehyde, zinc chloride and sodium cyanoborohydride in methanol. MS (ISP): 214.4 ([M+H]$^+$).

Example 22

(RS)-1-(1H-Imidazol-2-ylmethyl)-5-methoxy-2-methyl-2,3-dihydro-1H-indole

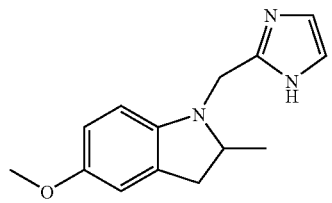

Analogously to Example 7, the above compound was obtained from 5-methoxy-2-methylindole and sodium cyanoborohydride in acetic acid, then treatment with imidazole-2-carboxaldehyde, zinc chloride and sodium cyanoborohydride in methanol. MS (ISP): 244.3 ([M+H]+).

Example 23

1-(1H-Imidazol-2-ylmethyl)-4-methoxy-2,3-dihydro-1H-indole

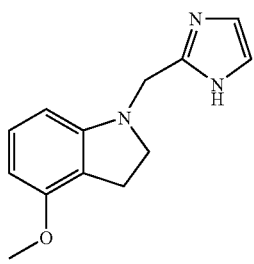

Analogously to Example 7, the above compound was obtained from 4-methoxyindole and sodium cyanoborohydride in acetic acid, then treatment with imidazole-2-carboxaldehyde, zinc chloride and sodium cyanoborohydride in methanol. MS (ISP): 230.3 ([M+H]+).

Example 24

7-Chloro-1-(1H-imidazol-2-ylmethyl)-2,3-dihydro-1H-indole

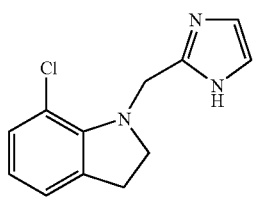

Analogously to Example 7, the above compound was obtained from 7-chloroindole and sodium cyanoborohydride in acetic acid, then treatment with imidazole-2-carboxaldehyde, zinc chloride and sodium cyanoborohydride in methanol. MS (ISP): 236.2 ([{$^{37}$Cl}M+H]+), 234.1 ([{$^{35}$Cl}M+H]+).

Example 25

6-Bromo-1-(H-imidazol-2-ylmethyl)-1,2,3,4-tetrahydro-quinoline

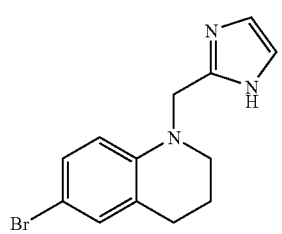

Analogously to Example 1, the above compound was obtained from 6-bromo-1,2,3,4-tetrahydro-quinoline, imidazole-2-carboxaldehyde, zinc chloride and sodium cyanoborohydride in methanol. MS (ISP): 294.1 ([{$^{81}$Br}M+H]+), 292.1 ([{$^{79}$Br}M+H]+).

Example 26

1-(1H-Imidazol-2-ylmethyl)-6-methyl-2,3-dihydro-1H-indole

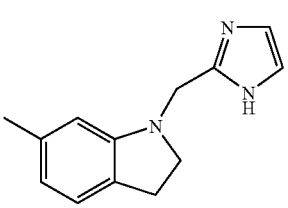

Analogously to Example 7, the above compound was obtained from 6-methylindole and sodium cyanoborohydride in acetic acid, then treatment with imidazole-2-carboxaldehyde, zinc chloride and sodium cyanoborohydride in methanol. MS (ISP): 214.4 ([M+H]+).

Example 27

(RS)-1-(1H-Imidazol-2-ylmethyl)-3-methyl-2,3-dihydro-1H-indole

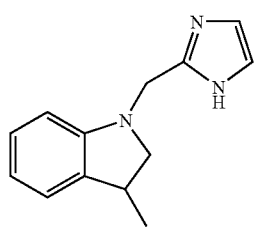

Analogously to Example 7, the above compound was obtained from (RS)-3-methylindole and sodium cyanoborohydride in acetic acid, then treatment with imidazole-2-carboxaldehyde, zinc chloride and sodium cyanoborohydride in methanol. MS (ISP): 214.3 ([M+H]⁺).

Example 28

5-Fluoro-1-(1H-imidazol-2-ylmethyl)-2,3-dihydro-1H-indole

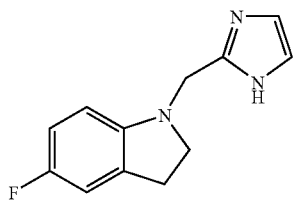

Analogously to Example 7, the above compound was obtained from 5-fluoroindole and sodium cyanoborohydride in acetic acid, then treatment with imidazole-2-carboxaldehyde, zinc chloride and sodium cyanoborohydride in methanol. MS (ISP): 218.3 ([M+H]⁺).

Example 29

6-Fluoro-1-(1H-imidazol-2-ylmethyl)-2,3-dihydro-1H-indole

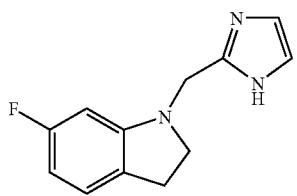

Analogously to Example 7, the above compound was obtained from 6-fluoroindole and sodium cyanoborohydride in acetic acid, then treatment with imidazole-2-carboxaldehyde, zinc chloride and sodium cyanoborohydride in methanol. MS (ISP): 218.4 ([M+H]⁺).

Example 30

5,6-Difluoro-1-(1H-imidazol-2-ylmethyl)-2,3-dihydro-1H-indole

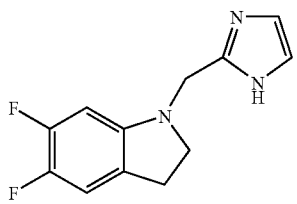

Analogously to Example 7, the above compound was obtained from 5,6-difluoroindole and sodium cyanoborohydride in acetic acid, then treatment with imidazole-2-carboxaldehyde, zinc chloride and sodium cyanoborohydride in methanol. MS (ISP): 236.1 ([M+H]⁺).

Example 31

(RS)-5-Fluoro-1-(1H-imidazol-2-ylmethyl)-2-methyl-2,3-dihydro-1H-indole

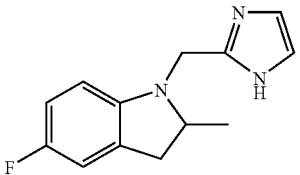

Analogously to Example 7, the above compound was obtained from (RS)-5-fluoro-2-methyl-indole and sodium cyanoborohydride in acetic acid, then treatment with imidazole-2-carboxaldehyde, zinc chloride and sodium cyanoborohydride in methanol. MS (ISP): 232.1 ([M+H]⁺).

Example 32

1-(1H-Imidazol-2-ylmethyl)-7-methyl-2,3-dihydro-1H-indole

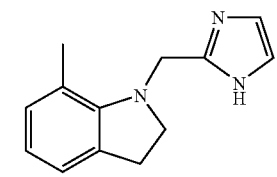

Analogously to Example 7, the above compound was obtained from 7-methyl-indole and sodium cyanoborohydride in acetic acid, then treatment with imidazole-2-carboxaldehyde, zinc chloride and sodium cyanoborohydride in methanol. MS (ISP): 214.3 ([M+H]⁺).

Example 33

1-(1H-Imidazol-2-ylmethyl)-4-methyl-2,3-dihydro-1H-indole

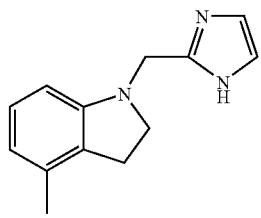

Analogously to Example 7, the above compound was obtained from 4-methyl-indole and sodium cyanoborohydride in acetic acid, then treatment with imidazole-2-carboxaldehyde, zinc chloride and sodium cyanoborohydride in methanol. MS (ISP): 214.3 ([M+H]⁺).

Example 34

(RS)-4-(1H-Imidazol-2-ylmethyl)-3-methyl-3,4-dihydro-2H-benzo[1,4]oxazine

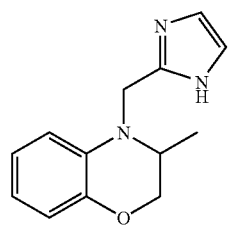

(a)
(RS)-3-Methyl-3,4-dihydro-2H-benzo[1,4]oxazine

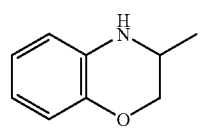

To a solution of 2H-1,4-benzoxazin-3(4H)-one (2.00 g, 13.4 mmol) in tetrahydrofuran (20 ml) was added dropwise at 5° C. a THF solution of methylmagnesium chloride (17.9 ml, 3 M, 53.7 mmol) and the reaction mixture was then stirred at 50° C. for 90 min. The reaction mixture was then cooled to 5° C. and quenched by dropwise addition of 20 ml acetic acid. Sodium borohydride (1.27 g, 33.5 mmol) was then added portionwise and the mixture was stirred at room temperature overnight. The resulting suspension was then cooled to 0° C. and 3 N aq. sodium hydroxide solution was added dropwise until the mixture was pH 10. Ethyl acetate was then added, the phases separated, and the organic phase dried over sodium sulphate and concentrated in vacuo. The residue was purified by chromatography on silica gel (eluant: heptane/ethyl acetate gradient) to yield the title compound as a colorless oil (0.92 g, 46%); MS (ISP): 150.3 ([M+H]$^+$).

(b) (RS)-4-(1H-Imidazol-2-ylmethyl)-3-methyl-3,4-dihydro-2H-benzo[1,4]oxazine

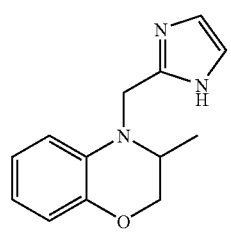

Prepared analogously to Example 1, from (RS)-3-methyl-3,4-dihydro-2H-benzo[1,4]oxazine, imidazole-2-carboxaldehyde, zinc chloride and sodium cyanoborohydride in methanol. MS (ISP): 230.4 ([M+H]$^+$).

Example 35

(RS)-2-Ethyl-1-(1H-imidazol-2-ylmethyl)-1,2,3,4-tetrahydro-quinoline

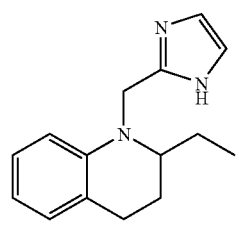

Analogously to Example 34, the above compound was obtained from 3,4-dihydro-2(1H)-quinolinone and ethylmagnesium chloride in tetrahydrofuran, then treatment with sodium borohydride in acetic acid and tetrahydrofuran, then treatment with imidazole-2-carboxaldehyde, zinc chloride and sodium cyanoborohydride in methanol. MS (ISP): 242.4 ([M+H]$^+$).

Example 36

1-(1H-Imidazol-2-ylmethyl)-6-methoxy-1,2,3,4-tetrahydro-quinoline

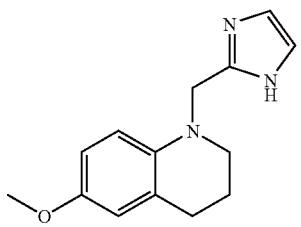

Analogously to Example 1, the above compound was obtained from 6-methoxy-1,2,3,4-tetrahydro-quinoline, imidazole-2-carboxaldehyde, zinc chloride and sodium cyanoborohydride in methanol. MS (ISP): 244.4 ([M+H]$^+$).

Example 37

1-(1H-Imidazol-2-ylmethyl)-7-methoxy-1,2,3,4-tetrahydro-quinoline

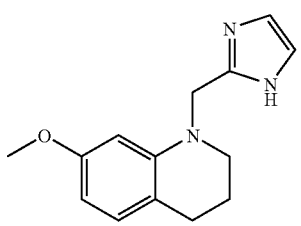

(a)
7-Hydroxy-3,4-dihydro-2H-quinoline-1-carboxylic acid tert-butyl ester

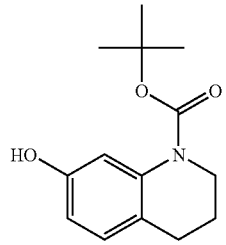

To a suspension of 1,2,3,4-tetrahydro-quinolin-7-ol (0.50 g, 3.35 mmol) in dichloromethane (40 ml) were added di-tert-butyldicarbonate (1.54 g, 7.04 mmol) and triethylamine (1.86 ml, 13.4 mmol) and the reaction mixture was stirred at 45° C. for 48 h. The mixture was then acidified to pH 6 by addition of 10% aq. citric acid solution and extracted with dichloromethane. The combined organic phases were washed with saturated brine, dried over sodium sulphate, and concentrated in vacuo. The residue was dissolved in methanol (40 ml) and aq. sodium hydroxide solution (6.70 ml, 13.4 mmol, 2 M) was added. After stirring for 16 h at 60° C., the mixture was cooled top room temperature and acidified to pH 6 by addition of 10% aq. citric acid solution and extracted with dichloromethane. The combined organic phases were dried over sodium sulphate and concentrated in vacuo to yield the title compound as a colourless oil which was used in the next step without further purification (0.33 g, 40%); MS (ISP): 250.3 ([M+H]$^+$), 194.4 ([M+H-Me$_2$C=CH$_2$]$^+$).

(b)
7-Methoxy-3,4-dihydro-2H-quinoline-1-carboxylic acid tert-butyl ester

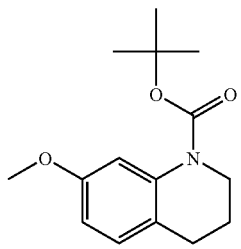

To a solution of 7-hydroxy-3,4-dihydro-2H-quinoline-1-carboxylic acid tert-butyl ester (120 mg, 0.48 mmol) in N,N-dimethylformamide (6 ml) was added sodium hydride (23 mg, 0.57 mmol, 60% dispersion in oil) and the reaction mixture was stirred at room temperature for 10 min. The mixture was then cooled to 0° C. and methyl iodide (0.04 ml, 0.64 mmol) was added dropwise. After stirring for 16 h at room temperature, the mixture was quenched by addition of water (10 ml) and extracted three times with ethyl acetate. The combined organic phases were washed with saturated brine, dried over sodium sulphate, and concentrated in vacuo. The residue was purified by chromatography on silica gel (eluant: heptane/ethyl acetate gradient) to yield the title compound as a colourless oil (52 mg, 41%); MS (ISP): 264.0 ([M+H]$^+$), 208.1 ([M+H-Me$_2$C=CH$_2$]$^+$).

(c) 7-Methoxy-1,2,3,4-tetrahydro-quinoline

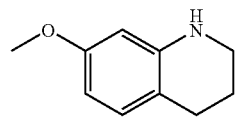

To a solution of 7-methoxy-3,4-dihydro-2H-quinoline-1-carboxylic acid tert-butyl ester (52 mg, 0.20 mmol) in dichloromethane (7 ml) at 0° C. was added dropwise trifluoroacetic acid (0.23 ml, 3.01 mmol) and the reaction mixture was then stirred at room temperature for 24 h. The mixture was then made basic to pH 9 by dropwise addition of saturated aq. sodium carbonate solution. The mixture was extracted three times with a 1:1 mixture of ethyl acetate and tetrahydrofuran, the phases separated, and the organic phase dried over sodium sulphate and concentrated in vacuo to yield the title compound as a light brown oil (37 mg, 92%); MS (ISP): 164.4 ([M+H]$^+$).

(d) 1-(1H-Imidazol-2-ylmethyl)-7-methoxy-1,2,3,4-tetrahydro-quinoline

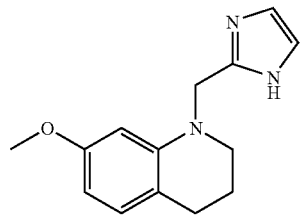

Prepared analogously to Example 1, from 7-methoxy-1,2,3,4-tetrahydro-quinoline, imidazole-2-carboxaldehyde, zinc chloride and sodium cyanoborohydride in methanol. MS (ISP): 244.4 ([M+H]$^+$).

Example 38

5-Benzyloxy-1-(1H-imidazol-2-ylmethyl)-1,2,3,4-tetrahydro-quinoline

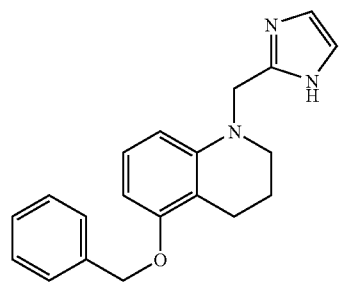

Analogously to Example 37, the above compound was obtained from 1,2,3,4-tetrahydro-quinolin-5-ol, di-tert-butyldicarbonate and triethylamine in dichloromethane, then

Example 39

7-Benzyloxy-1-(1H-imidazol-2-ylmethyl)-1,2,3,4-tetrahydro-quinoline

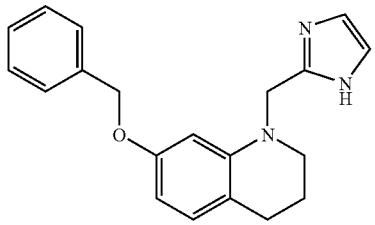

Analogously to Example 37, the above compound was obtained from 1,2,3,4-tetrahydro-quinolin-7-ol, di-tert-butyldicarbonate and triethylamine in dichloromethane, then treatment with sodium hydroxide in methanol, then treatment with benzyl bromide and sodium hydride in N,N-dimethylformamide, then treatment with trifluoroacetic acid, then treatment with imidazole-2-carboxaldehyde, zinc chloride and sodium cyanoborohydride in methanol. MS (ISP): 320.0 ([M+H]$^+$).

Example 40

7-Ethoxy-1-(1H-imidazol-2-ylmethyl)-1,2,3,4-tetrahydro-quinoline

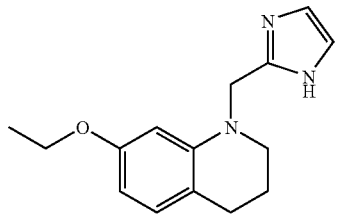

Analogously to Example 37, the above compound was obtained from 1,2,3,4-tetrahydro-quinolin-7-ol, di-tert-butyldicarbonate and triethylamine in dichloromethane, then treatment with sodium hydroxide in methanol, then treatment with iodoethane and sodium hydride in N,N-dimethylformamide, then treatment with trifluoroacetic acid, then treatment with imidazole-2-carboxaldehyde, zinc chloride and sodium cyanoborohydride in methanol. MS (ISP): 258.1 ([M+H]$^+$).

Example 41

1-(1H-Imidazol-2-ylmethyl)-7-isopropoxy-1,2,3,4-tetrahydro-quinoline

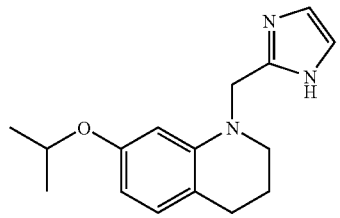

Analogously to Example 37, the above compound was obtained from 1,2,3,4-tetrahydro-quinolin-7-ol, di-tert-butyldicarbonate and triethylamine in dichloromethane, then treatment with sodium hydroxide in methanol, then treatment with 2-bromopropane and sodium hydride in N,N-dimethylformamide, then treatment with trifluoroacetic acid, then treatment with imidazole-2-carboxaldehyde, zinc chloride and sodium cyanoborohydride in methanol. MS (ISP): 272.5 ([M+H]$^+$).

Example 42

1-(1H-Imidazol-2-ylmethyl)-5-phenoxy-1,2,3,4-tetrahydro-quinoline

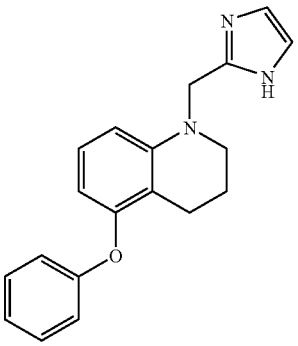

a) 5-Phenoxy-1,2,3,4-tetrahydro-quinoline

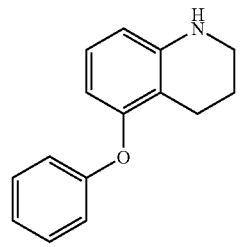

To a solution of 0.15 g (1.01 mmol) 1,2,3,4-tetrahydro-quinolin-5-ol in 10 ml dichloromethane were added 0.17 g (1.40 mmol) phenylboronic acid, 0.25 g (1.36 mmol) copper (II) acetate, a spatula end of 4 Å molecular sieves and 0.57 ml (4.52 mmol) triethylamine. The reaction mixture was stirred at room temperature for 72 h and then filtered through celite, washing with dichloromethane. The filtrate was concentrated in vacuo and the residue was purified by flash chromatography (silica gel, ethyl acetate/heptane gradient) to afford 34 mg (17%) of the title compound as a pink oil. MS (ISP): 226.3 ([M+H]$^+$).

(b) 1-(1H-Imidazol-2-ylmethyl)-5-phenoxy-1,2,3,4-tetrahydro-quinoline

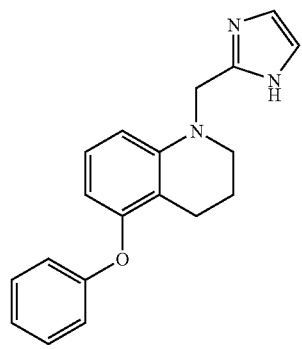

Prepared analogously to Example 1, from 5-phenoxy-1,2,3,4-tetrahydro-quinoline, imidazole-2-carboxaldehyde, zinc chloride and sodium cyanoborohydride in methanol. MS (ISP): 306.3 ([M+H]$^+$).

Example 43

1-(1H-Imidazol-2-ylmethyl)-7-phenoxy-1,2,3,4-tetrahydro-quinoline

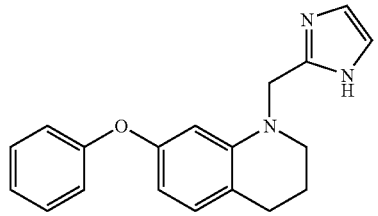

Analogously to Example 42, the above compound was obtained from 1,2,3,4-tetrahydro-quinolin-7-ol, phenylboronic acid, copper(II) acetate and triethylamine in dichloromethane, then treatment with imidazole-2-carboxaldehyde, zinc chloride and sodium cyanoborohydride in methanol. MS (ISP): 306.3 ([M+H]$^+$).

Example 44

The ability of the compounds of the present invention to bind to TAAR 1 was investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. (2005) *Genomics* 85, 372-385. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005) *Genomics* 85, 372-385. For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hours post transfection the culture medium was supplemented with 1 mg/ml G418 (Sigma, Buchs, Switzerland). After a culture period of about 10 days, clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Membrane Preparation and Radioligand Binding

Cells at confluence were rinsed with ice-cold phosphate buffered saline without Ca$^{2+}$ and Mg$^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. The cell pellet was then suspended in 20 ml HEPES-NaOH (20 mM), pH 7.4 containing 10 mM EDTA, and homogenized with a Polytron (PT 3000, Kinematica) at 10,000 rpm for 10 seconds. The homogenate was centrifuged at 48,000×g for 30 minutes at 4° C. and the pellet resuspended in 20 ml HEPES-NaOH (20 mM), pH 7.4 containing 0.1 mM EDTA (buffer A), and homogenized with a Polytron at 10,000 rpm for 10 seconds. The homogenate was then centrifuged at 48,000×g for 30 minutes at 4° C. and the pellet resuspended in 20 ml buffer A, and homogenized with a Polytron at 10,000 rpm for 10 seconds. Protein concentration was determined by the method of Pierce (Rockford, Ill.). The homogenate was then centrifuged at 48,000×g for 10 minutes at 4° C., resuspended in HEPES-NaOH (20 mM), pH 7.0 including MgCl$_2$ (10 mM) and CaCl$_2$ (2 ml) (buffer B) at 200 µg protein per ml and homogenized with a Polytron at 10,000 rpm for 10 seconds.

Binding assay was performed at 4° C. in a final volume of 1 ml, and with an incubation time of 30 minutes. The radioligand [$^3$H]-rac-2-(1,2,3,4-tetrahydro-1-naphthyl)-2-imidazoline was used at a concentration equal to the calculated K$_d$ value of 60 nM to give a total binding at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 pM-30 μM). The final dimethylsulphoxide concentration in the assay was 2%, and it did not affect radioligand binding. Each experiment was performed in duplicate. All incubations were terminated by rapid filtration through Uni-Filter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse on TAAR1 in the range of 0.02-0.20 as shown in the table below.

| Compound of Example | Ki (μM) mouse | Compound of Example | Ki |
|---|---|---|---|
| 1 | 0.0289 | 24 | 0.0557 |
| 4 | 0.055 | 25 | 0.0951 |
| 14 | 0.1958 | 26 | 0.129 |
| 15 | 0.0435 | 32 | 0.1729 |
| 16 | 0.035 | 33 | 0.1252 |
| 17 | 0.0362 | 38 | 0.0513 |
| 20 | 0.1182 | 42 | 0.0046 |
| 23 | 0.1148 | | |

The invention claimed is:

1. A compound according to formula I

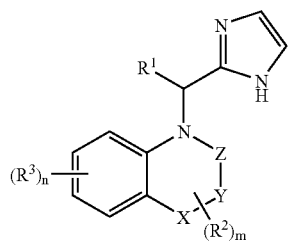

I wherein
$R^1$ is selected from the group consisting of hydrogen and lower alkyl;
each $R^2$ is independently selected from the group consisting of hydrogen and lower alkyl;
each $R^3$ is independently selected from the group consisting of hydrogen, lower alkyl, lower alkoxy, phenyloxy, benzyloxy, halogen and lower alkyl substituted by halogen;
X is selected from the group consisting of —$CH_2$—, —CH— and —O—;
Y is selected from the group consisting of —$CH_2$—, —CH— and a bond with the proviso that, when X is —O—, Y may not be a bond;
Z is selected from the group consisting of —$CH_2$— and —CH—;
m is 0, 1 or 2; and
n is 0, 1 or 2;
or a pharmaceutically-acceptable acid addition salt thereof.

2. A compound according to claim 1, wherein X is $CH_2$, Y is a bond and Z is $CH_2$.

3. A compound according to claim 2, selected from the group consisting of:
   1-(1H-imidazol-2-ylmethyl)-2,3-dihydro-1H-indole;
   5-bromo-1-(1H-imidazol-2-ylmethyl)-2,3-dihydro-1H-indole;
   7-ethyl-1-(1H-imidazol-2-ylmethyl)-2,3-dihydro-1H-indole;
   6-chloro-1-(1H-imidazol-2-ylmethyl)-2,3-dihydro-1H-indole;
   4-chloro-1-(1H-imidazol-2-ylmethyl)-2,3-dihydro-1H-indole;
   1-(1H-imidazol-2-ylmethyl)-7-methoxy-2,3-dihydro-1H-indole;
   1-(1H-imidazol-2-ylmethyl)-4-methoxy-2,3-dihydro-1H-indole;
   7-chloro-1-(1H-imidazol-2-ylmethyl)-2,3-dihydro-1H-indole;
   1-(1H-imidazol-2-ylmethyl)-6-methyl-2,3-dihydro-1H-indole;
   1-(1H-imidazol-2-ylmethyl)-7-methyl-2,3-dihydro-1H-indole; and
   1-(1H-imidazol-2-ylmethyl)-4-methyl-2,3-dihydro-1H-indole.

4. A compound according to claim 1, wherein X is CH, Y is a bond and Z is CH.

5. A compound according to claim 4, wherein said compound is (2RS,3RS)-1-(1H-imidazol-2-ylmethyl)-2,3-dimethyl-2,3-dihydro-1H-indole.

6. A compound according to claim 1, wherein X is $CH_2$, Y is $CH_2$ and Z is $CH_2$.

7. A compound according to claim 6, wherein said compound is selected from the group consisting of:
   6-bromo-1-(1H-imidazol-2-ylmethyl)-1,2,3,4-tetrahydro-quinoline;
   5-benzyloxy-1-(1H-imidazol-2-ylmethyl)-1,2,3,4-tetrahydro-quinoline; and
   1-(1H-imidazol-2-ylmethyl)-5-phenoxy-1,2,3,4-tetrahydro-quinoline.

8. A compound according to claim 1, wherein X is —O—, Y is $CH_2$ and Z is $CH_2$.

9. A compound according to claim 8, wherein said compound is 4-(1H-imidazol-2-ylmethyl)-3,4-dihydro-2H-benzo[1,4]oxazine.

10. A compound according to claim 1, wherein X is —O—, Y is $CH_2$ and Z is CH.

11. A compound according to claim 10, wherein said compound is (RS)-4-(1H-imidazol-2-ylmethyl)-3-methyl-3,4-dihydro-2H-benzo[1,4]oxazine.

12. A process for the preparation of a compound of formula I-1

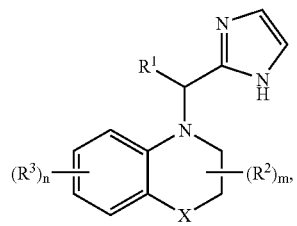

I-1 said process comprising reductively aminating a compound of formula II

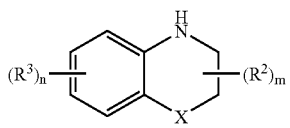

and a compound of formula III

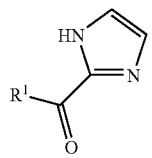

wherein, in the above formulas,
- $R^1$ is selected from the group consisting of hydrogen and lower alkyl;
- each $R^2$ is independently selected from the group consisting of hydrogen and lower alkyl;
- each $R^3$ is independently selected from the group consisting of hydrogen, lower alkyl, lower alkoxy, phenyloxy, benzyloxy, halogen and lower alkyl substituted by halogen;
- X is selected from the group consisting of —$CH_2$—, —CH— and —O—;
- m is 0, 1 or 2; and
- n is 0, 1 or 2.

13. A pharmaceutical composition comprising a therapeutically effective amount of a compound of formula I

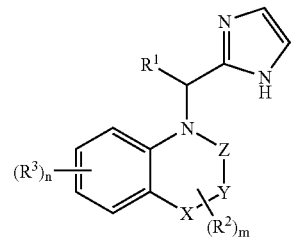

wherein
- $R^1$ is selected from the group consisting of hydrogen and lower alkyl;
- each $R^2$ is independently selected from the group consisting of hydrogen and lower alkyl;
- each $R^3$ is independently selected from the group consisting of hydrogen, lower alkyl, lower alkoxy, phenyloxy, benzyloxy, halogen and lower alkyl substituted by halogen;
- X is selected from the group consisting of —$CH_2$—, —CH— and —O—;
- Y is selected from the consisting of —$CH_2$—, —CH— and a bond with the proviso that, when X is —O—, Y may not be a bond;
- Z is selected from the group consisting of —$CH_2$—and —CH—;
- m is 0, 1 or 2; and
- n is 0, 1 or 2;

or a pharmaceutically-acceptable acid addition salt thereof and a pharmaceutically acceptable excipient.

* * * * *